US010813721B2

(12) United States Patent
Sterental et al.

(10) Patent No.: US 10,813,721 B2
(45) Date of Patent: Oct. 27, 2020

(54) SYSTEMS AND METHOD FOR MANAGEMENT AND DELIVERY OF ORTHODONTIC TREATMENT

(71) Applicant: Align Technology, Inc., San Jose, CA (US)

(72) Inventors: Rene Sterental, Palo Alto, CA (US); Lou Shuman, Chevy Chase, MD (US); Maia Singer, Campell, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 406 days.

(21) Appl. No.: 14/717,229

(22) Filed: May 20, 2015

(65) Prior Publication Data
US 2015/0254410 A1 Sep. 10, 2015

Related U.S. Application Data

(63) Continuation of application No. 11/760,689, filed on Jun. 8, 2007, now Pat. No. 9,060,829.

(51) Int. Cl.
A61C 7/08 (2006.01)
G09B 23/28 (2006.01)
G16H 50/20 (2018.01)
G16H 50/50 (2018.01)
A61C 7/00 (2006.01)

(52) U.S. Cl.
CPC .............. A61C 7/08 (2013.01); G09B 23/28 (2013.01); G16H 50/20 (2018.01); G16H 50/50 (2018.01); A61C 7/002 (2013.01)

(58) Field of Classification Search
CPC ....... A61C 7/002; A61C 7/00; G06F 19/3437; G06F 19/321
See application file for complete search history.

(56) References Cited

U.S. PATENT DOCUMENTS

| | | | |
|---|---|---|---|
| 2,467,432 | A | 4/1949 | Kesling |
| 3,407,500 | A | 10/1968 | Kesling |
| 3,600,808 | A | 8/1971 | Reeve |
| 3,660,900 | A | 5/1972 | Andrews |

(Continued)

FOREIGN PATENT DOCUMENTS

| | | | |
|---|---|---|---|
| AU | 3031677 | A | 5/1979 |
| AU | 517102 | B2 | 7/1981 |

(Continued)

OTHER PUBLICATIONS

American Association for Dental Research, Summary of Activities, Mar. 20-23, 1980, Los ngeles, CA, p. 195.

(Continued)

Primary Examiner — Joseph D Burgess
(74) Attorney, Agent, or Firm — Wilson Sonsini Goodrich & Rosati

(57) ABSTRACT

The present invention provides systems and methods of managing delivery of an orthodontic treatment plan using treatment guidelines, instructions and appointment planning tools customized to the individual patient being treated. A method includes, e.g., generating a treatment plan for a patient, generating a customized set of treatment guidelines, providing the set of customized treatment guidelines to the practitioner; and providing a set of orthodontic appliances to the practitioner.

20 Claims, 7 Drawing Sheets

(56) References Cited

U.S. PATENT DOCUMENTS

| | | |
|---|---|---|
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbate et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemehen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasniek et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,752,832 A | 5/1998 | Vardimon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,067,523 A | 5/2000 | Bair et al. |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,406,292 B1 | 6/2002 | Chishti et al. |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,074,038 B1 | 7/2006 | Miller |
| 7,077,647 B2 | 7/2006 | Choi et al. |
| 7,156,661 B2 | 1/2007 | Choi et al. |

(56) References Cited

U.S. PATENT DOCUMENTS

| | | |
|---|---|---|
| 7,357,636 B2 | 4/2008 | Hedge et al. |
| 7,474,307 B2 | 1/2009 | Chishti et al. |
| 7,970,628 B2 | 6/2011 | Kuo et al. |
| 8,075,306 B2 | 12/2011 | Kitching et al. |
| 8,562,338 B2 | 10/2013 | Kitching et al. |
| 8,636,510 B2 | 1/2014 | Kitching et al. |
| 8,899,978 B2 | 12/2014 | Kitching et al. |
| 9,017,072 B2 | 4/2015 | Kitching et al. |
| 9,060,829 B2 | 6/2015 | Sterental et al. |
| 9,364,297 B2 | 6/2016 | Kitching et al. |
| 1,005,217 A1 | 8/2018 | Kitching et al. |
| 1,034,263 A1 | 7/2019 | Kitching et al. |
| 2001/0002310 A1* | 5/2001 | Chishti ............... A61C 7/00 433/24 |
| 2002/0006597 A1 | 1/2002 | Andreiko et al. |
| 2002/0010568 A1 | 1/2002 | Rubbert et al. |
| 2002/0064746 A1 | 5/2002 | Muhammad et al. |
| 2002/0072027 A1 | 6/2002 | Chishti |
| 2002/0150855 A1* | 10/2002 | Shishti ............... G06T 17/10 433/6 |
| 2003/0009252 A1 | 1/2003 | Pavlovskaia et al. |
| 2003/0049584 A1 | 3/2003 | Chishti et al. |
| 2003/0139834 A1 | 7/2003 | Nikolskiy et al. |
| 2003/0143509 A1 | 7/2003 | Kopelman et al. |
| 2003/0190575 A1 | 10/2003 | Hilliard |
| 2003/0224311 A1 | 12/2003 | Cronauer |
| 2004/0072120 A1 | 4/2004 | Lauren |
| 2004/0128010 A1 | 7/2004 | Pavlovskaia et al. |
| 2004/0197727 A1 | 10/2004 | Sachdeva et al. |
| 2004/0202983 A1 | 10/2004 | Tricca et al. |
| 2005/0038669 A1 | 2/2005 | Sachdeva et al. |
| 2005/0048432 A1 | 3/2005 | Choi et al. |
| 2005/0055118 A1 | 3/2005 | Nikolskiy et al. |
| 2005/0089822 A1 | 4/2005 | Geng |
| 2005/0192835 A1 | 9/2005 | Kuo et al. |
| 2005/0241646 A1 | 11/2005 | Sotos et al. |
| 2005/0271996 A1 | 12/2005 | Sporbert et al. |
| 2006/0004609 A1 | 1/2006 | Kenneth et al. |
| 2006/0079981 A1 | 4/2006 | Rubbert et al. |
| 2006/0121408 A1 | 6/2006 | Hedge et al. |
| 2006/0127836 A1 | 6/2006 | Wen |
| 2006/0147872 A1 | 7/2006 | Andreiko |
| 2006/0194163 A1 | 8/2006 | Tricca et al. |
| 2006/0199142 A1 | 9/2006 | Liu et al. |
| 2006/0263739 A1 | 11/2006 | Sporbert et al. |
| 2006/0286501 A1 | 12/2006 | Chishti et al. |
| 2007/0003900 A1 | 1/2007 | Miller |
| 2007/0072144 A1 | 3/2007 | Imgrund et al. |
| 2007/0099147 A1 | 5/2007 | Sachdeva et al. |
| 2007/0184398 A1 | 8/2007 | Cronauer |
| 2007/0226005 A1* | 9/2007 | Smith ............... G06F 19/322 705/2 |
| 2008/0050692 A1 | 2/2008 | Hilliard |
| 2008/0305451 A1 | 12/2008 | Kitching et al. |
| 2008/0305452 A1 | 12/2008 | Sterental et al. |
| 2008/0305453 A1 | 12/2008 | Kitching et al. |
| 2008/0305454 A1 | 12/2008 | Kitching et al. |
| 2008/0306724 A1 | 12/2008 | Kitching et al. |
| 2012/0225401 A1 | 9/2012 | Kitching et al. |
| 2014/0023980 A1 | 1/2014 | Kitching et al. |
| 2014/0193765 A1 | 7/2014 | Kitching et al. |
| 2014/0335466 A1 | 11/2014 | Kitching et al. |
| 2016/0074138 A1 | 3/2016 | Kitching et al. |
| 2019/0008612 A1 | 1/2019 | Kitching et al. |
| 2020/0093569 A1 | 3/2020 | Kitching et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO-2006065955 A2 | 6/2006 |
| WO | WO-2006118771 A2 | 11/2006 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

(56) References Cited

OTHER PUBLICATIONS

Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk To The Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.

Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Henson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulating-stressputonfa...>.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).

(56) References Cited

OTHER PUBLICATIONS

Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984). Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, Oct. 22-23, 1990.

Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.

(56) References Cited

OTHER PUBLICATIONS

Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances—Pro Lab product information for patients, 2 pages (2002).
European search report with written opinion dated Mar. 7, 2017 for EP16197945.5.
Richmond, et al. A 2-Center Comparison of Orthodontist's Perceptions of Orthodontic Treatment Difficulty. Jan. 2001, Angle Orthodontist, vol. 71, No. 5, pp. 404-410.
Co-pending U.S. Appl. No. 16/852,251, filed Apr. 17, 2020.

\* cited by examiner

FIG. 5A

Patient: Test5791131 00Jodawith2PS3516939769

CLINASSIST SERVICE

RETURN TO VIP  PRINT invisalign

ClinCheck Appointment Planning

| Treatment Plan | Appointment | Appointment 2 | Appointment 3 | Appointment 4 |

Overview

Setup Notes:
SPECIFIC INFORMATION
* Adjustments to the posterior occlusion have been made according to your request.

IPR Prescription:
- 0.2mm between teeth #4 and #5
- 0.2mm between teeth #10 and #11
- 0.4mm between teeth #12 and #13

Attachment Prescription:
- Tooth #4
- Tooth #5
- Tooth #6
- Tooth #10
- Tooth #11
- Tooth #12
- Tooth #13
- Tooth #20
- Tooth #21
- Tooth #28
- Tooth #29

Initial number of progress impressions required: 2.
(may change based on progress evaluation)

View Controls
Click on the interior icons to view the corresponding image, or click on "View All" to view all as a composite

Rotate Controls
Horizontal  Vertical

Resize Controls
Zoom Out  Zoom In 0.2 mm between tooth #10 and #11 [entire treatment]

Interproximal Reduction Instructions  Show  Hide
Attachments  Show  Hide

Estimated Duration
26-39 aligners
(52-78 weeks)

Ready

SYSTEMS AND METHOD FOR MANAGEMENT AND DELIVERY OF ORTHODONTIC TREATMENT

CROSS-REFERENCES TO RELATED APPLICATIONS

This application is a continuation of U.S. patent application Ser. No. 11/760,689, filed Jun. 8, 2007, now U.S. Pat. No. 9,060,829, the full disclosure of which is incorporated herein by reference in its entirety.

The present application is related to U.S. application Ser. No. 11/760,705, entitled "Treatment Progress Tracking And Recalibration," filed on Jun. 8, 2007, now U.S. Pat. No. 8,562,338, U.S. application Ser. No. 11/760,701, entitled "Treatment Planning And Progress Tracking Systems and Methods," filed on Jun. 8, 2007 and U.S. application Ser. No. 11/760,612, entitled "System And Method For Detecting Deviations During The Course Of An Orthodontic Treatment To Gradually Reposition Teeth," filed on Jun. 8, 2007, now U.S. Pat. No. 8,562,338, the full disclosures of which are incorporated herein by reference in their entirety.

BACKGROUND OF THE INVENTION

The present invention relates generally to the field of orthodontics, and more particularly to systems and methods of managing delivery of an orthodontic treatment plan using treatment guidelines, instructions and appointment planning tools customized to the individual patient being treated.

An objective of orthodontics is to move a patient's teeth to positions where function and/or aesthetics are optimized. Traditionally, appliances such as braces are applied to the patient's teeth by an orthodontist and the set of braces exerts continual force on the teeth and gradually urges them toward their intended positions. Over time and with a series of clinical visits and adjustments to the braces, the orthodontist eventually adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

Recent advances in orthodontic treatment, including availability of the treatment systems discussed above, have made orthodontic treatment options available to a wide variety of patients and dental practitioners. Unfortunately, barriers to more wide-spread use of such treatment options still exist, thereby preventing both patients and dental practitioners from access to orthodontic treatment technology they desire. One such barrier includes more wide-spread use of orthodontic treatment technology to dental practitioners with limited experience in orthodontics. For example, many general dental practitioners with limited knowledge or exposure to orthodontics may be interested in learning orthodontic techniques and providing such treatment to patients, but may lack confidence in their abilities to effectively deliver treatment and/or achieve predictable outcomes. Accordingly, improved methods and techniques are needed for facilitating orthodontic practice among practitioners with limited experience in orthodontics and will enhance treatment options and improve efficacy in patients in need of such treatment.

BRIEF SUMMARY OF THE INVENTION

The present invention provides improved systems and methods of managing delivery of an orthodontic treatment plan using treatment guidelines, instructions and appointment planning tools customized to the individual patient being treated. The customized information provided according to the present invention can be offered in support or addition to orthodontic treatment systems currently available, and additionally provides to a treating practitioner specifically customized and tailored appointment guidelines and instructions regarding recommended patient/practitioner appointments as well as specific tasks that should be accomplished at identified appointments. Information and guidelines according to the invention techniques provides numerous advantages in that they provide more customized and specific guidelines and instructions for administering treatment and can be used, for example, to more effectively manage delivery of orthodontic treatment and increase treatment efficacy. For example, the inventive techniques more advantageously assist certain practitioners, including those that may lack experience and/or confidence in delivering orthodontic treatment or may be concerned about an ability to achieve a predictable or desired outcome in orthodontic care, as well as practitioners desiring more customized guidelines for a given treatment plan.

Thus, in one aspect, the present invention provides methods and systems of managing delivery of an orthodontic treatment plan. Such a method can include generating a treatment plan for a patient, generating a customized set of treatment guidelines, e.g., corresponding to a phase of the treatment plan, and providing the set of customized treatment guidelines as well as a set of orthodontic appliances to the practitioner. Systems for managing delivery of an orthodontic treatment plan is provided. A system can include a computer coupled to a server, the computer comprising a processor and a computer readable medium. The computer readable medium of the system can include instructions which, if executed, cause the computer to generate a treatment plan for a patient, generate a set of customized treatment guidelines, and generate digital models for each appliance of a set of orthodontic appliances for treating the patient according to the treatment plan.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 5A is a screen shot showing a graphical representation of electronically provided guidelines according to another embodiment of the present invention.

DETAILED DESCRIPTION OF THE INVENTION

Figure 1:
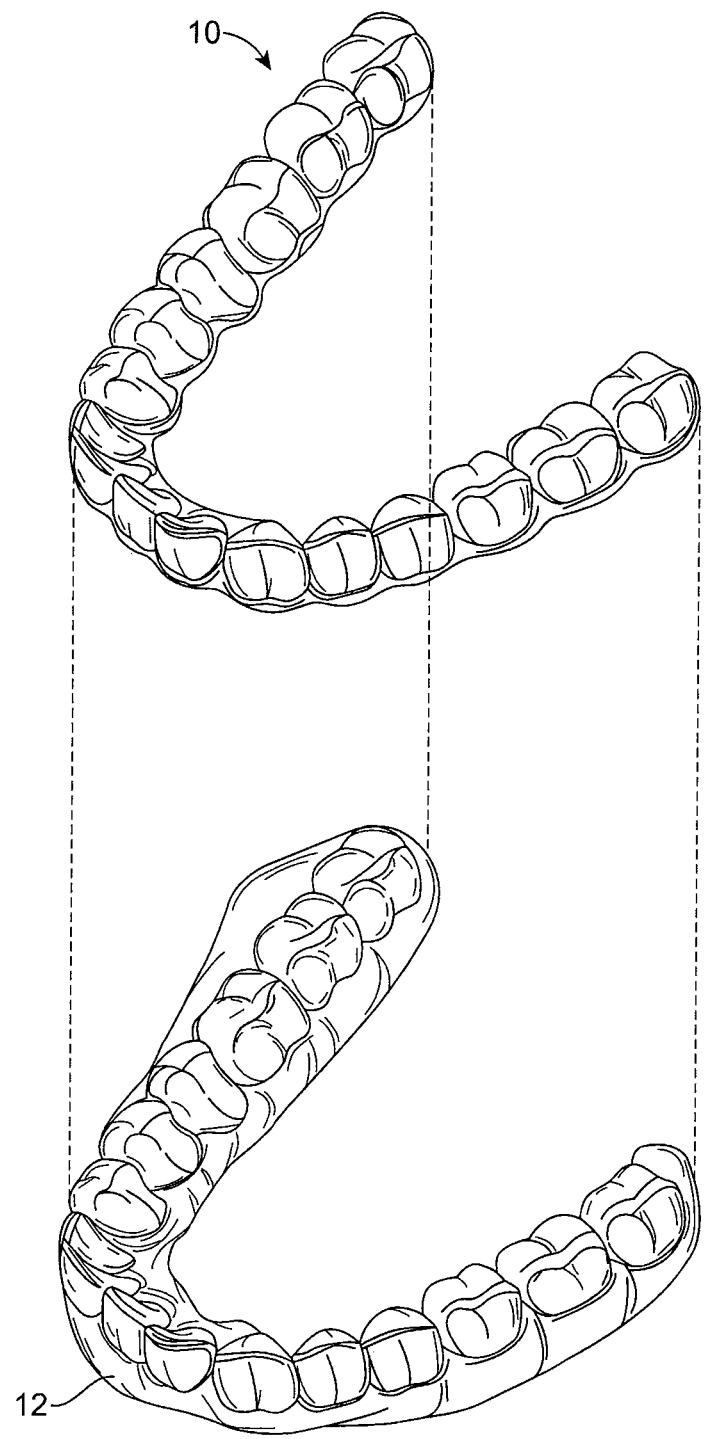
FIG. 1 illustrates a jaw together with an incremental positioning adjustment appliance according to an embodiment of the present invention.

The present invention provides improved systems and methods of managing delivery of an orthodontic treatment plan using treatment guidelines, instructions and appointment planning tools customized to the individual patient being treated. The systems and methods of the present invention include generating a treatment plan for a patient and additionally producing one or more sets of treatment guidelines specifically customized to the patient being treated. The customized treatment guidelines are designed to be provided to a dental practitioner in order to provide enhanced instruction and guidance for delivering the orthodontic treatment to the patient. By customizing the guidelines to the specific patient, the present invention advantageously assists certain practitioners, including those that may lack experience and/or confidence in delivering orthodontic treatment or may be concerned about an ability to achieve a predictable or desired outcome in orthodontic care, and additionally enhances treatment efficacy.

Systems and methods of managing delivery of an orthodontic treatment plan using treatment guidelines, instructions and appointment planning tools customized to the individual patient according to the present invention can be included in a variety of orthodontic treatment regimens. For example, the customized instructions and appointment planning tools can be optionally included and incorporated into other aspects of treatment according to the Invisalign® System. Treatment can be pre-planned for administering to a patient in a series of one or more phases, with at least some of the phases each including a set of appliances that are worn successively by the patient to reposition the teeth through planned arrangements and eventually toward a selected final arrangement. As treatment will typically be planned as a series of treatment phases, the planned phases can each include customized treatment guidelines tailored to that particular phase, which are useful in helping manage delivery and treatment of the patient with the set of appliances. In this way, customized appointment planning and instruction according to the present invention can be integrated with the orthodontic treatment process for improved treatment delivery and/or efficacy.

As set forth above, customized set of treatment guidelines can be provided to the practitioner and designed to correspond to a particular phase of the treatment plan, which can include a corresponding set of appliances that are administered to the patient. Along with the set(s) of appliances that provided to the treating practitioner according to a treatment phase, the practitioner will receive a copy of a customized set of treatment guidelines that will identify all the recommended and/or necessary appointments as well as corresponding instructions or tasks to be completed at each of the appointments. The particular appointments, general or specific timing of the appointments, as well as specific tasks that should be performed at each appointment are customized to the individual patient and typically account for patient-specific factors such as the positioning of the patient's teeth, desired movements, treatment goals, and other clinical considerations.

The present system and methods can by used along with any orthodontic treatment methodology, including patient removable appliances as well as fixed appliances such as more traditional orthodontic brackets and wires, and can even include other dental treatments. More typically, systems and methods of the present invention will be used in conjunction with patient removable, incremental adjustment appliances. FIG. 1 shows one adjustment appliance 10 which is worn by the patient in order to achieve an incremental repositioning of individual teeth in the jaw 12 as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance for a set period of time or until the pressure of each appliance on the teeth is minimal or can no longer be felt. A plurality of different appliances (e.g., set) can be designed and even fabricated prior to the patient wearing any appliance of the plurality. At that point, the patient replaces the current adjustment appliance with the next adjustment appliance in the series until no more appliances remain. The appliances are generally not affixed to the teeth so as to require removal by a practitioner (e.g., patient removable) and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 2:
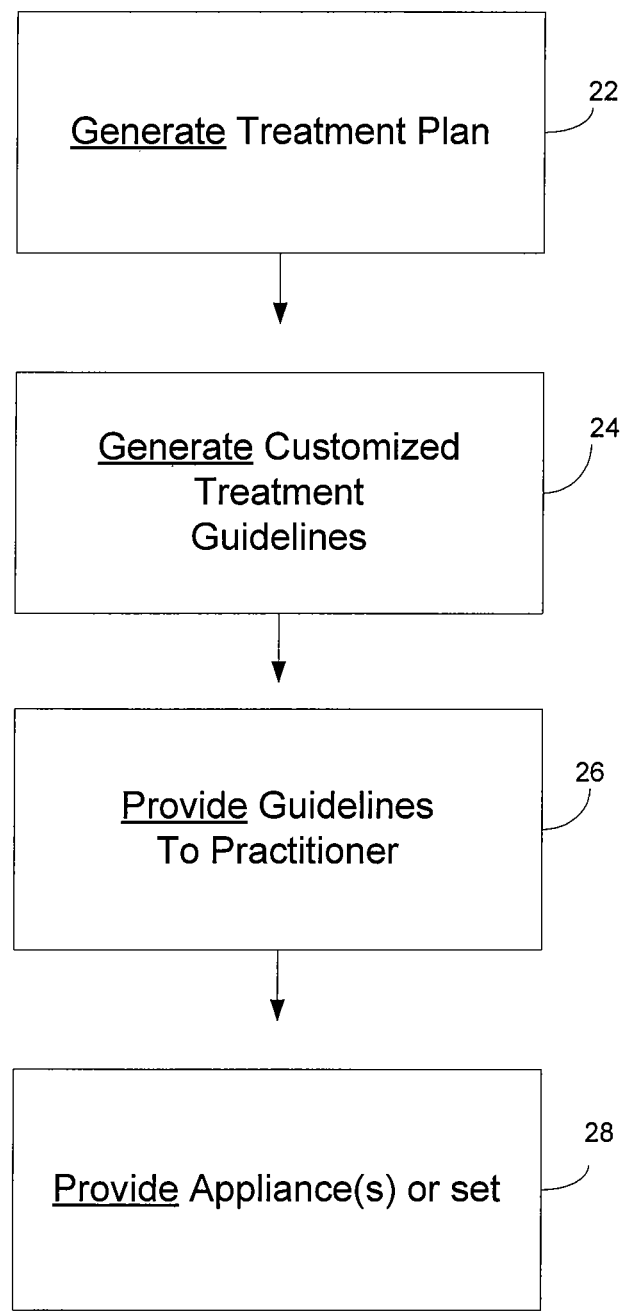
FIG. 2 includes a flow chart illustrating managing delivery of an orthodontic treatment plan including customized treatment guidelines according to an embodiment of the present invention.

Referring to FIG. 2, a process 20 according to the present invention is illustrated. Individual aspects of the process are discussed in further detail below. The process includes generating a treatment plan for repositioning a patient's teeth (Step 22). Briefly, a treatment plan will include obtaining data comprising an initial arrangement of the patient's teeth, which typically includes obtaining an impression or scan of the patient's teeth prior to the onset or start of treatment. The treatment plan will also include identifying a desired final arrangement of the patients teeth, as well as a plurality of planned successive or intermediary tooth arrangements for moving the teeth along a treatment path from the initial arrangement toward the selected final arrangement. As noted, treatment can be pre-planned for administration to a patient in a series of one or more treatment phases, with a phase including a set of appliances that are worn successively by the patient to reposition the teeth through planned arrangements and eventually toward a selected final arrangement. The process further includes proactively generating customized treatment guidelines (Step 24), which can be subsequently provided to the practitioner (Step 26). The treatment plan includes multiple phases of treatment, with a customized set of treatment guidelines generated that correspond to a phase of the treatment plan. The guidelines will include detailed information on timing and/or content (e.g., specific tasks) to be completed during a given phase of treatment, and will be of sufficient detail to guide a less experienced practitioner, or practitioner relatively new to the particular orthodontic treatment process, through the phase of treatment. The process further includes providing or delivering the customized treatment guidelines to the practitioner (Step 26) so as to help instruct the practitioner as how to deliver a given phase of treatment. As set forth above, appliances can be generated based on the planned arrangements and will be provided to the practitioner and ultimately administered to the patient (Step 28). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of treatment guidelines, or appliances and guidelines can be provided separately.

Figure 3:
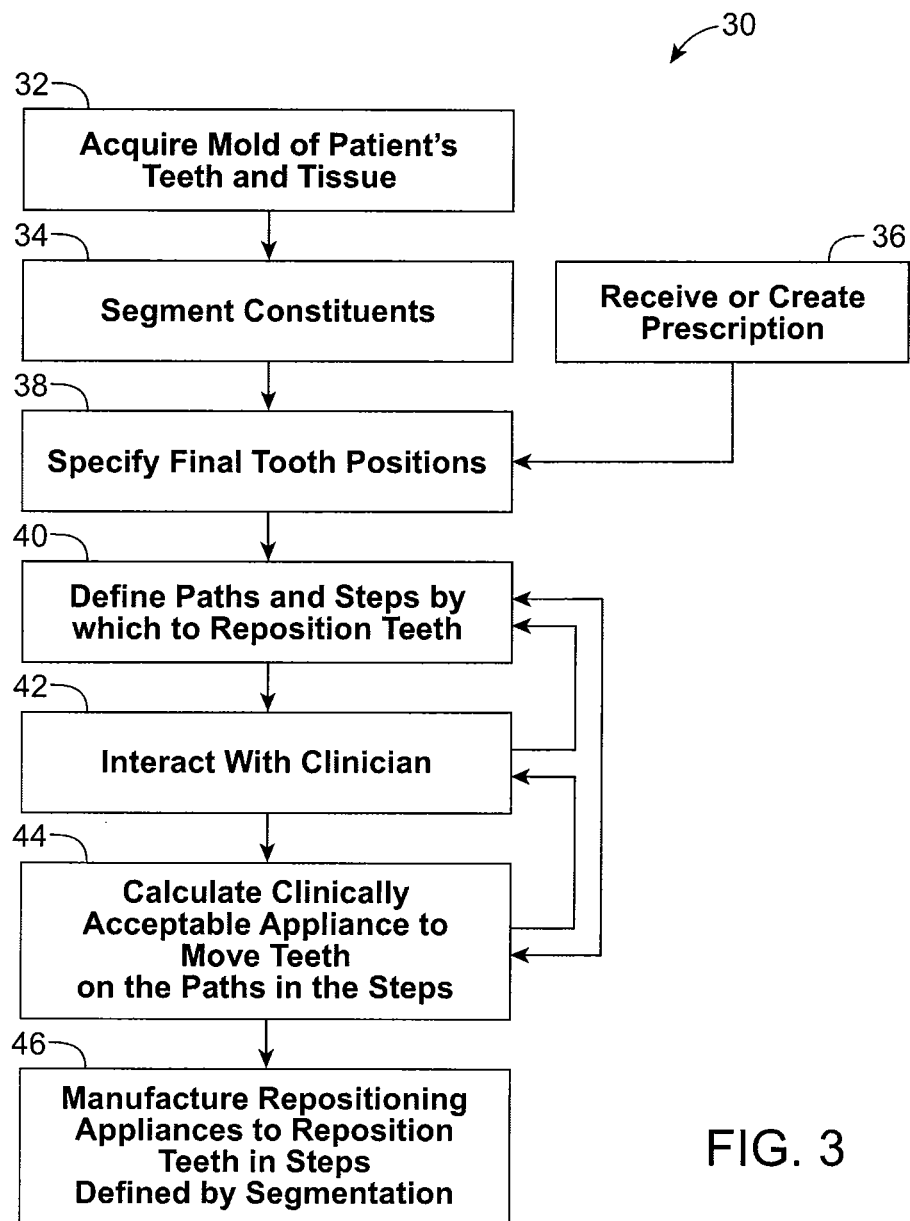
FIG. 3 shows generating a treatment plan according to an embodiment of the present invention.

FIG. 3 illustrates the general flow of an exemplary process 30 for defining and generating a treatment plan, including repositioning appliances for orthodontic treatment of a patient. The steps of the process can be implemented as computer program modules for execution on one or more computer systems.

As an initial step, a mold or a scan of patient's teeth or mouth tissue is acquired (Step 32). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 34), including defining discrete dental objects. For example, data structures that digitally represent individual tooth crowns can be produced. In some embodiments, digital models of entire teeth are produced, including measured or extrapolated hidden surfaces and root structures.

Desired final position of the teeth, or tooth positions that are desired and/or intended end result of orthodontic treatment, can be received, e.g., from a clinician in the form of a prescription, can be calculated from basic orthodontic principles, or can be extrapolated computationally from a clinical prescription (Step 36). With a specification of the desired final positions of the teeth and a digital representation of the teeth themselves, the final position and surface geometry of each tooth can be specified (Step 38) to form a complete model of the teeth at the desired end of treatment. The result of this step is a set of digital data structures that represents a desired and/or orthodontically correct repositioning of the modeled teeth relative to presumed-stable tissue. The teeth and tissue are both represented as digital data.

Having both a beginning position and a final position for each tooth, the process next defines a treatment path or tooth path for the motion of each tooth (Step 40). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interact with a clinician responsible for the treatment of the patient (Step 42). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 44). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician (Step 42).

Having calculated appliance definitions, the process 30 can proceed to the manufacturing step (Step 46) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases it might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to inspect the progression of the patient's teeth along the treatment path before manufacturing and/or administering subsequent set(s) of appliances.

Generating and/or analyzing digital treatment plans, as discussed herein, can include, for example, use of 3-dimensional orthodontic treatment planning tools such as ClinCheck® from Align Technology, Inc. or other software available from eModels and OrthoCAD, among others. These technologies allow the clinician to use the actual patient's dentition as a starting point for customizing the treatment plan. The ClinCheck® technology uses a patient-specific digital model to plot a treatment plan, and then uses a processed (e.g., segmented) scan of the achieved treatment outcome to assess the degree of success of the outcome as compared to the original digital treatment plan as, as discussed in U.S. Pat. Nos. 7,156,661 and 7,077,647 (see also, below).

As set forth above, once a treatment plan is in place the present invention includes generating customized treatment guidelines that can be provided to the dental practitioner for facilitating administration of treatment and improving desired treatment outcomes. Since the treatment plan typically includes a series of one or more treatment phases, a customized set of treatment guidelines will be generated and will typically include a set of guidelines corresponding to each phase of the treatment plan. Treatment guidelines are provided to the practitioner for administration of treatment to the patient. Since a phase(s) of treatment can include a set of appliances to be administered to the patient, treatment guidelines can be provided to the practitioner concurrently with a set of appliances, or appliances and guidelines can be provided separately. Guidelines can include, for example, hard copies (e.g., paper copies) printed and shipped to the practitioner, or can include one or more electronic copies transmitted to the practitioner over a network, for example, by email or by incorporation into other network-based treatment planning tools (e.g., ClinCheck®).

As a treatment plan will typically include a series of one or more appointments, guidelines will typically include one or more recommended patient/practitioner appointments that may include suggested timing for the appointments. Suggested timing can be specific and may more particularly identify a date or specific date range for scheduling one or more appointments, or can be more generalized and for each appointment may list a broader timing range (e.g., 1 week appointment, 2 week, 3 week, etc.). Appointment timing can be identified to coincide with another treatment event, such as administering an appliance or set of appliance, or wearing of an appliance(s) by the patient for a period of time. Guidelines corresponding to a particular appointment can include a list of recommended tasks to be completed during the practitioner's appointment with the patient. Non-exclusive examples of general tasks that may need to be performed at a given appointment can include appliance delivery and administration to the patient; tooth modifications such as extractions, interproximal reduction (IPR), periodontal evaluation, and the like; placement/removal of attachment(s); auxiliary placement; general monitoring and compliance; treatment progress tracking; finishing appointment or finalization of treatment (e.g., refinement evaluation or final impression and/or order retainer); retainer administration to the patient; retainer maintenance; cleaning appointments; etc. Since the guidelines provided to the practitioner will be specifically customized to the individual patient, the guidelines will not only include identification of the tasks to be completed but will typically include specific details and/or instructions, customized to the individual patient, that will help guide the practitioner through the identified tasks during an appointment with the patient. In some instances, the information provided in the customized guidelines can be further tailored to the practitioner to provide the appropriate level of detail, content, and the like. For example, information provided to the practitioner, such as amount of detail in the identified tasks, can be selected based on the experience level of the practitioner or preferences of the practitioner, e.g., including preferences specified by the practitioner.

As set forth above, guidelines can include, for example, hard copies (e.g., paper copies) printed and shipped to the practitioner, or can include one or more electronic copies transmitted to the practitioner over a network. In addition to recommended appointments, recommended tasks, and specific instructions or guidance on how tasks may be completed, guidelines according to the present invention can include additional information and/or details that can further facilitate a practitioner in administering treatment to the patient, such as support contact information, direction to additional training materials, product ordering information, and the like. For example, where guidelines are provided electronically, such as on-line, additional materials can include one or more hyperlinks, such as JIT troubleshooting links, support links and/or numbers, e-mail links, order placement links, links to ClinCheck sharing modules, training modules or information, etc.

Figure 4:
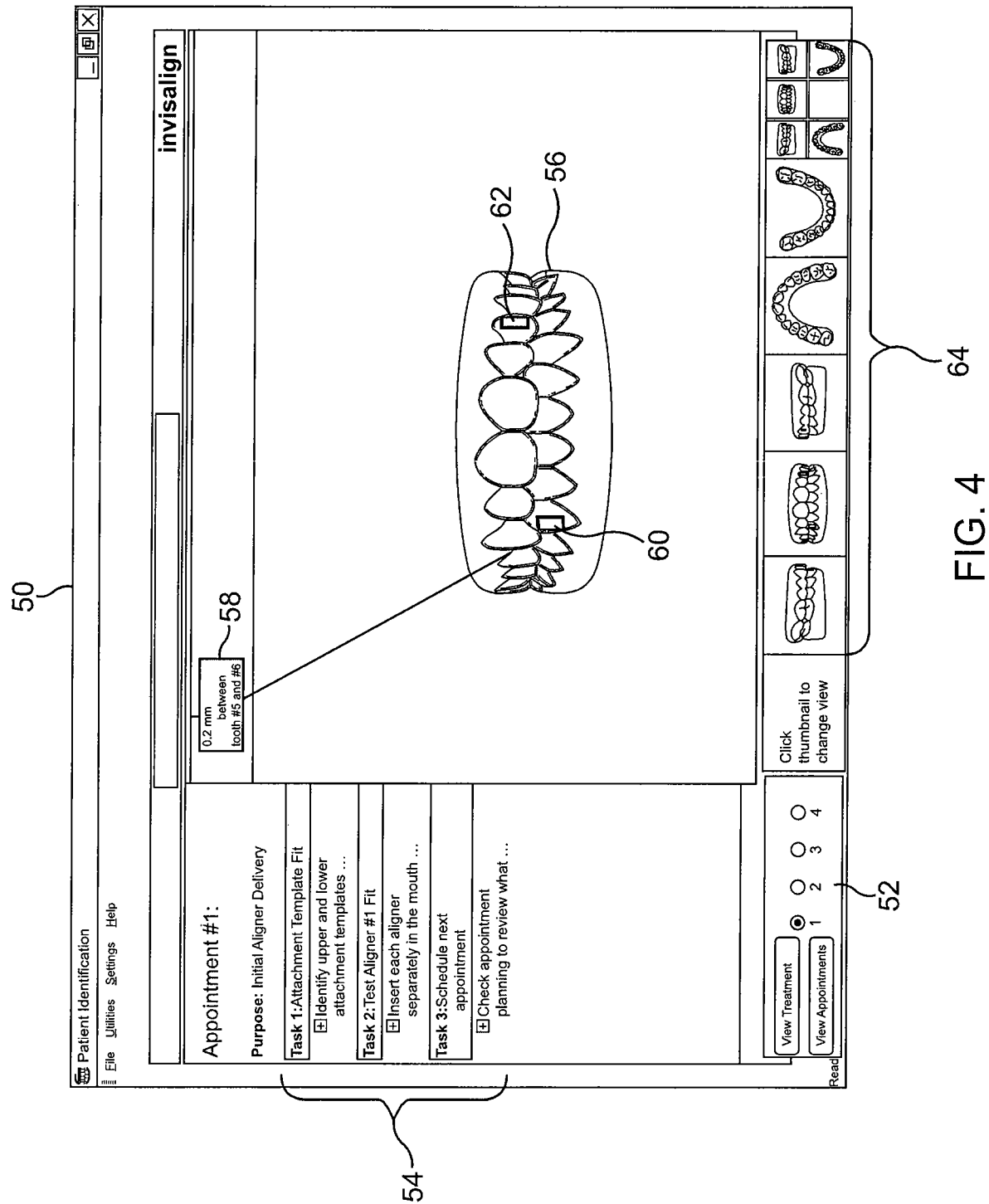
FIG. 4 is a screen shot illustrating a graphical representation of electronically provided guidelines corresponding to a treatment plan according to an embodiment of the present invention.

FIG. 4 shows a screen shot 50 illustrating a graphical representation of electronically provided guidelines corresponding to a treatment plan according to an embodiment of the present invention. A user can select a given appointment (example "Appointment #1" is illustrated) from an appointment menu 52 and customized set of treatment guidelines 54 are displayed corresponding to the selected appointment. The guidelines 54 can include a general description of the selected appointment (e.g., "purpose") so as to communicate to the practitioner general goals to be accomplished at the appointment. The guidelines 54 can further include a list of specific tasks to be completed. Specific tasks can be selected by the practitioner for further viewing of more specific details, such as by selecting a drop down menu that provides more detailed and specific instructions to guide the practitioner through administration of the tasks. For a given appointment, a graphical representation of the patient's projected arrangement of teeth 56 at a given appointment/time can be provided and incorporated into the interface for delivering the guidelines or task instructions. For example, as shown, specific identification 58 of interproximal reduction areas may be shown and can contain details on the reduction to be performed. Attachment locations 60, 62 can also be illustrated on the representation 56 to facilitate treatment administration. Additional views 64 (e.g., thumbnail views) of the patients teeth can also be provided for selection by the practitioner. Providing the guidelines and instructions along with such graphical illustrations can advantageously help to more effectively communicate task instructions to the practitioner at the appropriate treatment time and more effectively manage treatment.

FIG. 5A shows a screen shot 65 illustrating a graphical representation of electronically provided guidelines according to another embodiment of the present invention. As above, a user can select a given appointment (e.g., "Appointment 1", "Appointment 2", etc.) from an appointment menu 66 (e.g., appointment menu bar) for viewing of information including customized guidelines corresponding to the selected appointment. Additionally, the appointment menu 66 can include an option to select an overview or general information on the treatment plan in general, which can be graphically represented as a treatment plan overview tab 67 in the menu 66. Selection of the overview 67 can further display overview information 68 providing information on the treatment plan in general. Information 68 can include, for example, a list of tasks to be completed throughout the treatment (or portion thereof) of the patient. Specifically identified task may be linked to other files so as to provide additional detailed information on a given task upon selection. As above, a graphical representation 69 of the patient's teeth can be presented illustrating projected tooth positions at a given time or appointment.

Figure 5B:
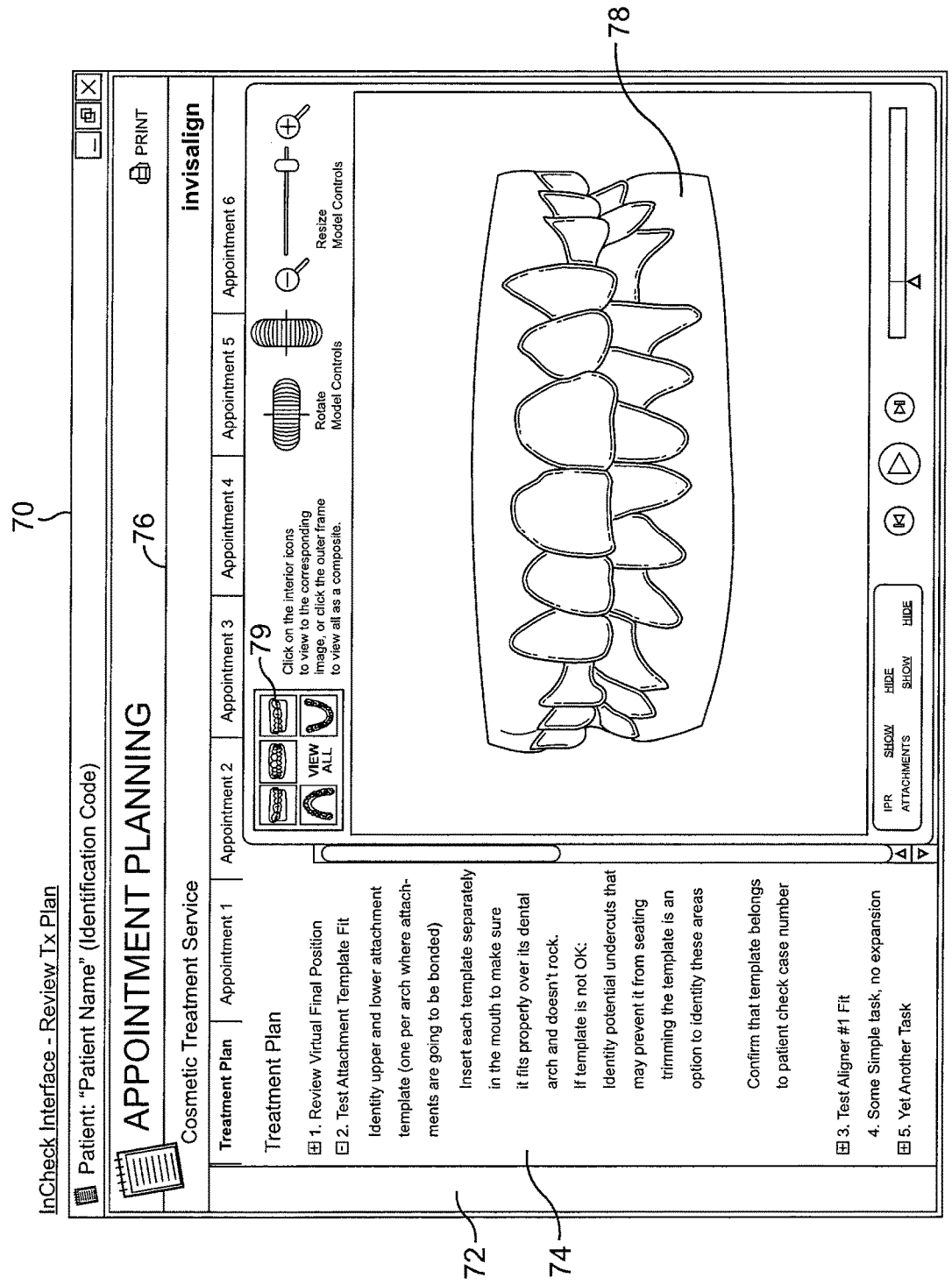
FIG. 5B is a screen shot showing a graphical representation of electronically provided guidelines corresponding to a treatment plan according to another embodiment of the present invention.

FIG. 5B shows a screen shot 70 illustrating a graphical representation of electronically provided guidelines corresponding to a treatment plan according to another embodiment of the present invention. Customized treatment guidelines 72 are shown provided according to the treatment plan. As above, drop down options 74 are provided that allow the practitioner to select a given task in order to view more detailed instructions and information for guidance on how to administer the task. The practitioner can toggle between various appointments by using an appointment menu 76 (e.g., menu bar), where a given appointment according to the treatment plan can be selected, thereby providing a list of corresponding tasks to be completed at the selected appointment. Additionally, a graphical representation 78 of the patient's projected tooth arrangement at a given appointment or time can be displayed and may include a view menu 79 for selecting different graphical views of the patients teeth. Additional animation and/or instructions can be included or incorporated into a graphical representation of the patient's teeth to further communicate treatment guidelines and tasks.

Figure 6:
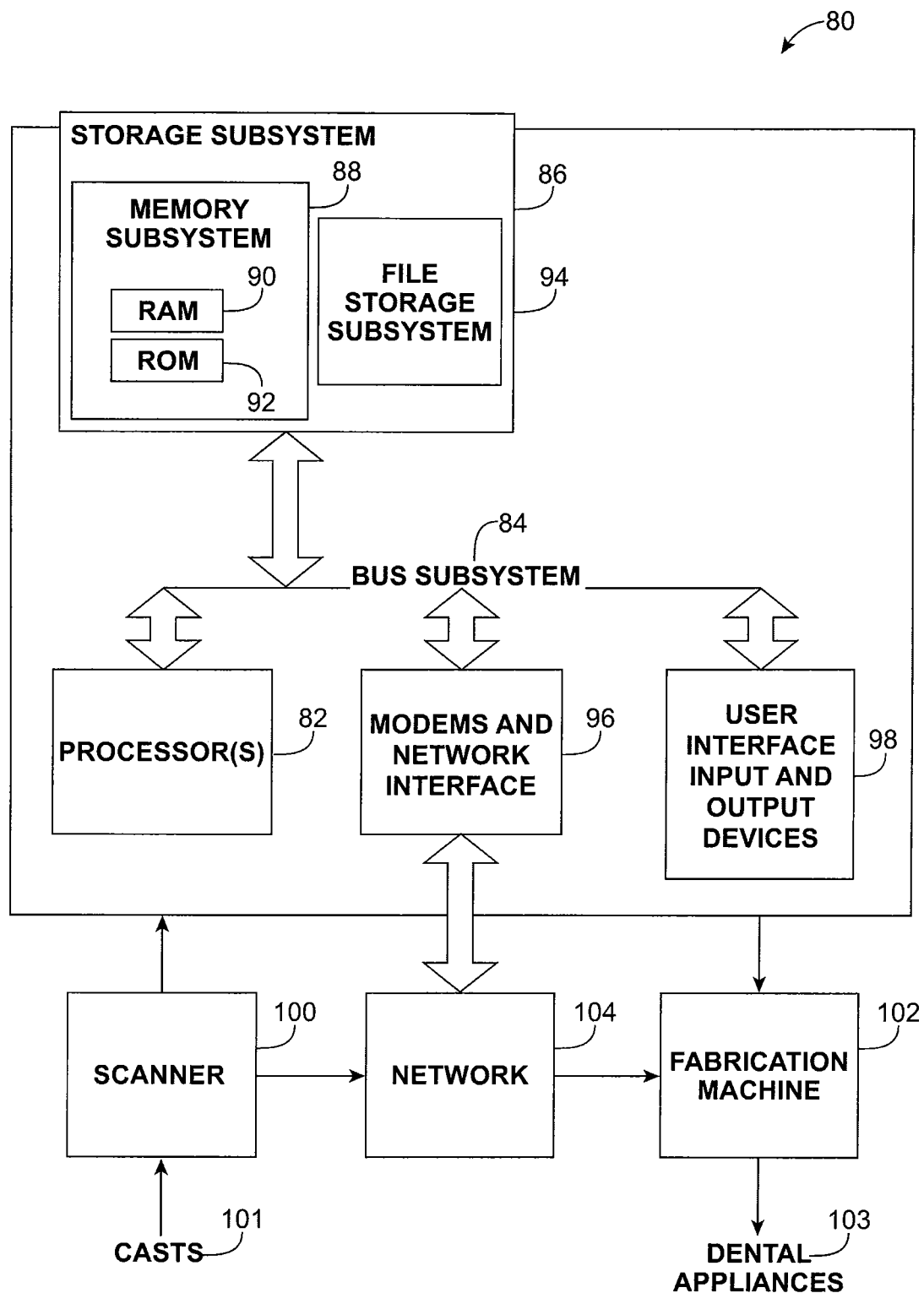
FIG. 6 is a block diagram illustrating a system for generating appliances in accordance with methods and processes of the present invention.

FIG. 6 is a simplified block diagram of a data processing system 80 that may be used in executing methods and processes described herein. The data processing system 80 typically includes at least one processor 82 that communicates with a number of peripheral devices via bus subsystem 84. These peripheral devices typically include a storage subsystem 86 (memory subsystem 88 and file storage subsystem 94), a set of user interface input and output devices 98, and an interface to outside networks 96, including the public switched telephone network. This interface is shown schematically as "Modems and Network Interface" block 96, and is coupled to corresponding interface devices in other data processing systems via communication network interface 104. Data processing system 80 can include, for example, one or more computers, such as a personal computer, workstation, mainframe, and the like.

The user interface input devices 98 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 86 maintains the basic required programming, including computer readable media having instructions (e.g., operating instructions, etc.), and data constructs. The program modules discussed herein are typically stored in storage subsystem 86. Storage subsystem 86 typically comprises memory subsystem 88 and file storage subsystem 94. Memory subsystem 88 typically includes a number of memories (e.g., RAM 90, ROM 92, etc.) including computer readable memory for storage of fixed instructions, instructions and data during program execution, basic input/output system, etc. File storage subsystem 94 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 100 includes any means for obtaining an image of a patient's teeth, some of which have been described herein above, which can be obtained either from the patient or from treating professional, such as an orthodontist, and includes means of providing the image data/information to data processing system 80 for further processing. In some embodiments, scanner 100 may be located at a location remote with respect to other components of the system and can communicate image data and/or information to data processing system 80, for example, via a network interface 104. Fabrication system 102 fabricates dental appliances based on a treatment plan, including data set information received from data processing system 80. Fabrication machine 102 can, for example, be located at a remote location and receive data set information from data processing system 80 via network interface 104.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A system for determining recommended timing for administration of at least one orthodontic appliance to a patient's teeth, the system comprising:
   one or more processors; and
   memory comprising instructions that, when executed by the one or more processors, cause the system to:
      receive scan data including a representation of a surface of the patient's teeth;
      segment the scan data to define digital representations of individual teeth of the patient's teeth;
      generate a plurality of digital models of the patient's teeth based on the digital representations of individual teeth, each of the plurality of digital models corresponding to one of a plurality of planned intermediate stages of successive tooth arrangements for moving the patient's teeth along a treatment path from an initial arrangement toward a selected final arrangement in a series of phases of treatment including at least a first phase of treatment and a second phase of treatment; and
      generate, before fabrication and administration of the at least one orthodontic appliance based on the plurality of digital models, a first customized recommended timing for administration of at least one orthodontic appliance of a plurality of orthodontic appliances to the patient's teeth during the first phase of treatment, the first customized recommended timing being a duration between a first consecutive two stages of the plurality of planned intermediate stages, and wherein the plurality of orthodontic appliances are shaped to move the patient's teeth at least partially along the treatment path from the initial arrangement toward the selected final arrangement and the first customized recommended timing being based on first desired movements of the patient's teeth and first treatment goals and second customized recommended timing for administration of at least one orthodontic appliance of a plurality of orthodontic appliances to the patient's teeth during the second phase of treatment, the second customized recommended timing being a duration between a second consecutive two stages of the plurality of planned intermediate stages, and wherein the plurality of orthodontic appliances are shaped to move the patient's teeth at least partially along the treatment path from the initial arrangement toward the selected final arrangement and the second customized recommended timing being based on second desired movements of the patient's teeth and second treatment goals.

2. The system of claim 1, further comprising a display, wherein the instructions further cause the system to generate customized treatment guideline data based on the plurality of digital models, the customized treatment guideline data including the first and second customized recommended timing and the display being configured to display the customized treatment guideline data.

3. The system of claim 2, wherein the display is configured to display a graphical representation of a projected tooth arrangement corresponding to the one of the plurality of planned intermediate stages of successive tooth arrangements.

4. The system of claim 2, wherein the customized treatment guideline data further comprises recommended timing for one or more treatment events.

5. The system of claim 4, wherein the one or more treatment events comprise a tooth modification, the tooth modification comprising one or more of an extraction, interproximal reduction (IPR), placement of an attachment, or removal of an attachment.

6. The system of claim 4, wherein the one or more treatment events comprise one or more of tracking treatment progress, finalization of treatment, administration of a retainer, or cleaning.

7. The system of claim 4, wherein the customized treatment guideline data comprises instructions for performing the one or more treatment events.

8. The system of claim 2, wherein the first and second customized recommended timing comprises appointment timing for scheduling one or more appointments for completing one or more treatment tasks, the one or more treatment tasks comprising the administration of the at least one orthodontic appliance.

9. The system of claim 8, the display being configured to provide a user interface wherein the user interface is configured to display the appointment timing for the one or more appointments and the one or more treatment tasks to be completed at the one or more appointments.

10. The system of claim 1, wherein the instructions further cause the system to generate fabrication instructions for manufacturing the plurality of orthodontic appliances based on the plurality of digital models, wherein the fabrication instructions are generated prior to administration of any of the plurality of orthodontic appliances to the patient's teeth.

11. A method for determining recommended timing for administration of at least one orthodontic appliance to a patient's teeth, the method comprising:
receiving scan data including a representation of a surface of the patient's teeth;
segmenting the scan data to define digital representations of individual teeth of the patient's teeth;
generating, with one or more processing devices, a plurality of digital models of the patient's teeth based on the digital representations of individual teeth, each of the plurality of digital models corresponding to one of a plurality of planned intermediate stages of successive tooth arrangements for moving the patient's teeth along a treatment path from an initial arrangement toward a selected final arrangement in a series of phases of treatment including at least a first phase of treatment and a second phase of treatment; and
generating before fabrication and administration of the at least one orthodontic appliance based on the plurality of digital models, with the one or more processing devices, a first customized recommended timing for administration of at least one orthodontic appliance of a plurality of orthodontic appliances to the patient's teeth during the first phase of treatment, the first customized recommended timing being a duration between a first consecutive two stages of the plurality of planned intermediate stages, and wherein the plurality of orthodontic appliances are shaped to move the patient's teeth at least partially along the treatment path from the initial arrangement toward the selected final arrangement and the first customized recommended timing being based on first desired movements of the patient's teeth and first treatment goals and a second customized recommended timing for administration of at least one orthodontic appliance of a plurality of orthodontic appliances to the patient's teeth during the second phase of treatment, the second customized recommended timing being a duration between a second consecutive two stages of the plurality of planned intermediate stages, and wherein the plurality of orthodontic appliances are shaped to move the patient's teeth at least partially along the treatment path from the initial arrangement toward the selected final arrangement and the second customized recommended timing being based on second desired movements of the patient's teeth and second treatment goals.

12. The method of claim 11, further comprising displaying customized treatment guideline data on a display, the customized treatment guideline data based on the plurality of digital models and including the first and second customized recommended timing.

13. The method of claim 12, wherein displaying the customized treatment guideline data comprises displaying a graphical representation of a projected tooth arrangement corresponding to one of the plurality of planned intermediate stages of successive tooth arrangements.

14. The method of claim 12, wherein the customized treatment guideline data further comprises recommended timing for one or more treatment events.

15. The method of claim 14, wherein the one or more treatment events comprise a tooth modification, the tooth modification comprising one or more of an extraction, interproximal reduction (IPR), placement of an attachment, or removal of an attachment.

16. The method of claim 14, wherein the one or more treatment events comprise one or more of tracking treatment progress, finalization of treatment, administration of a retainer, or cleaning.

17. The method of claim 14, wherein the customized treatment guideline data comprises instructions for performing the one or more treatment events.

18. The method of claim 12, wherein the first and second customized recommended timing comprises appointment timing for scheduling one or more appointments for completing one or more treatment tasks, the one or more treatment tasks comprising the administration of the at least one orthodontic appliance.

19. The method of claim 18, further comprising providing a user interface on the display, wherein the user interface is configured to display the appointment timing for the one or more appointments and the one or more treatment tasks to be completed at the one or more appointments.

20. The method of claim 11, further comprising generating, with the one or more processors, fabrication instructions for manufacturing the plurality of orthodontic appliances based on the plurality of digital models, wherein the fabrication instructions are generated prior to administration of any of the plurality of orthodontic appliances to the patient's teeth.

* * * * *